United States Patent
Brewer et al.

(10) Patent No.: US 6,425,395 B1
(45) Date of Patent: Jul. 30, 2002

(54) DETERMINATION OF MASK FITTING PRESSURE AND CORRECT MASK FIT

(75) Inventors: Gregory Newton Brewer, Lewisham; Gregory Alan Colla, North Sydney; Steven Paul Farrugia, Lugarno; Chinmayee Somaiya, Dundas Valley, all of (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/469,954

(22) Filed: Dec. 21, 1999

(30) Foreign Application Priority Data

Dec. 21, 1998 (AU) .............................................. PP7831

(51) Int. Cl.[7] .............................................. A61M 16/00
(52) U.S. Cl. .............................. 128/202.22; 128/204.18; 128/204.21; 128/204.23
(58) Field of Search ....................... 128/204.18, 202.22, 128/204.21, 204.23

(56) References Cited

U.S. PATENT DOCUMENTS

| | | | |
|---|---|---|---|
| 4,846,166 A | * 7/1989 | Willeke | 128/200.24 |
| 5,289,819 A | * 3/1994 | Kroger et al. | 128/200.24 |
| 5,313,937 A | * 5/1994 | Zdorjkowski | 128/202.22 |
| 5,540,219 A | * 7/1996 | Mechlenberg et al. | 128/204.23 |
| 5,632,269 A | * 5/1997 | Zdrojkowski | 128/204.23 |
| 5,803,065 A | * 9/1998 | Zdrojkowski et al. | 128/204.23 |
| 5,823,187 A | 10/1998 | Estes et al. | |
| 5,860,418 A | * 1/1999 | Lundberg | 128/202.22 |
| 5,901,704 A | 5/1999 | Estes et al. | |
| 5,970,975 A | * 10/1999 | Estes et al. | 128/204.23 |

FOREIGN PATENT DOCUMENTS

| WO | WO 87/02898 | 5/1987 |
|---|---|---|
| WO | WO 96/03174 | 2/1996 |

* cited by examiner

Primary Examiner—John G. Weiss
Assistant Examiner—Mital Patel
(74) Attorney, Agent, or Firm—Pillsbury & Winthrop LLP

(57) ABSTRACT

A CPAP treatment apparatus, as one form of positive pressure ventilatory assistance, includes a turbine/blower, operated by a mechanically coupled electrical motor that receives air or breathable gas at an inlet thereof, and supplies the breathable gas at a delivery pressure to a delivery tube/hose having a connection at the other end thereof with a nose mask. A microcontroller has an operational "Mask-Fit" mode. An initial constant pressure level is applied by the blower to the mask. If the functional mode is a manual mode, then the mask-fit test pressure is the current 'set' pressure. If the functional mode is the automatic titration mode, the mask-fit test pressure is the $95^{th}$ percentile pressure of the previous session, otherwise it is the base treatment pressure, e.g. 10–12 cm $H_2O$. This constant pressure is applied for a period of time, typically 1–3 minutes. The microcontroller continuously determines mask leak as the value, $f_{LEAK}$, from a flow sensor, comparing this to a threshold, and providing the patent with a visual indication of degree of leak. In this way the patient can manipulate the mask to ensure correct fitting as indicated by the appropriate message or indication.

12 Claims, 3 Drawing Sheets

DETERMINATION OF MASK FITTING PRESSURE AND CORRECT MASK FIT

FIELD OF THE INVENTION

The invention relates to the determination of a suitable pressure to test for correct mask fitting, and for correct mask fit.

BACKGROUND OF THE INVENTION

Sleep disordered breathing, such as Obstructive Sleep Apnea (OSA), is treated with devices which provide positive pressure ventilatory assistance, such as Continuous Positive Airway Pressure (CPAP) devices. A typical device comprises a controllable flow generator coupled to a nasal mask that provides a supply of breathable gas to a patient in the range 4 to 30 cm $H_2O$ positive pressure. Furthermore, a field of ventilatory assistance known as noninvasive positive pressure ventilation (NIPPV) supplies a patient with various pressures at appropriate times during the patient's breathing cycle. Throughout this specification a reference to "CPAP" or "ventilatory assistance apparatus" is to be understood as including a reference to CPAP or non-invasive positive pressure ventilation. Nasal prongs, a mouth mask or fill face mask may be used as alternatives to a nasal mask. A reference to a mask herein is intended to include a reference to any of these patient interface devices.

Apparatus, and thus treatment efficacy depends on correct mask fitting to reduce or eliminate leaks. A known arrangement of CPAP apparatus (for example) provides a test mode, which may be used prior to the functional (or operational) mode, whereby be user can test-fit the mask. Whilst in this test mode, the apparatus provides a test pressure. This test pressure may be, for example, fixed at 10 cm $H_2O$ or alternatively the maximum output pressure of the device. During this test mode the mask is fitted to the patient so as to avoid leaks that might occur at the test pressure.

Another known arrangement is that the mask test pressure is chosen to be a function of the minimum and maximum pressure settings. For example:

$$\text{Mask-fit test pressure} = P_{min\_set} + 0.75(P_{max\_set} - P_{min\_set}) \quad (1)$$

where $P_{min\_set}$ = Minimum pressure setting $P_{max\_set}$ = Maximum pressure setting The problem with these known methods is that the test pressure will be independent of the pressures actually delivered during an automatically titrating mode. During the automatically titrating mode (or autotreatment mode) the device varies the pressure delivered in the mask in accordance with the patient's requirements while the patient sleeps. Examples of devices and methods of treatment that operate in such an automatic mode can be found in commonly owned U.S. Pat. No. 5,704,345 (Berthon-Jones assigned to ResMed Limited) and WO 98/12965 (Berthon-Jones assigned to ResMed Limited).

A good indication of mask fitting under normal conditions of use will not be obtained if the test pressure is significantly different to the pressures encountered in normal use. No leaks may be detected during the test mode, but during the functional mode, the mask may leak. Alternatively, the mask-fit test pressure may be unnecessarily high and discourage the patient from using the mask-fit feature, or from using the device due to the discomfort resulting from the test pressure suggesting that the patient fit the mask with a strap tension that is greater than would be necessary in practice.

FIG. 1 shows a cumulative frequency plot for overnight treatment using an automatically titrating CPAP device for two patients, (A'__',B'-.-.-'), together with the 95th percentile (- - - - -). The sampling rate was 1 per minute. For patient A, there were 375 pressure readings and the 95th percentile pressure was approximately 7 cm$H_2O$. For patient B, there were 79 pressure readings and the 95th percentile pressure was approximately 20 cm $H_2O$. If the prior art solution using equation (1) had been adopted, with the 4 cm and 20 cm minimum and maximum pressure settings respectively, the mask-fit pressure would have been 16 cm $H_2O$. This pressure is much higher than necessary for patient A, and may have been insufficient for patient B.

DISCLOSURE OF THE INVENTION

It is an object of the invention to overcome or at least ameliorate these problems, achieved by providing for the adaptive determination of the mask-fit test pressure based on prior use.

The invention discloses a method for determining a mask-fit test pressure to be applied to a wearer's mask by ventilatory assistance apparatus, the method comprising the step of:

determining a percentile pressure of a previous ventilatory assistance session to be said test pressure.

The invention further discloses a method for assessing correct fitting of a mask delivering ventilatory assistance, provided by ventilatory assistance apparatus, to a wearer of the mask, the method comprising the steps of:

determining a percentile pressure of a previous ventilatory assistance session to be applied as a test pressure;

determining leak flow from said mask at the test pressure; and displaying or otherwise indicating the magnitude of the leak flow as an indication of correct mask fitting.

The invention further discloses ventilatory assistance apparatus comprising:

a controllable flow generator providing a positive pressure of breathable gas;

a conduit coupled to the flow generator to receive said gas;

a mask to be worn by a wearer, in turn, to receive said gas from said conduit at a desired pressure; and a controller having control of said flow generator, and operable to cause a mask-fit test pressure to be applied at the mask, said test pressure being determined as a percentile pressure of a previous ventilatory assistance session.

The invention yet further discloses ventilatory assistance apparatus as defined above, further comprising:

flow sensor means, for sensing respiratory flow, passing a flow signal to the controller; and display or indication means; and wherein the controller is further operable to determine mask leak flow at the test pressure from the respiratory flow signal, and to cause the display or indication means to display or otherwise indicate the magnitude of the leak flow as an indication of correct mask fitting.

It is preferred that the indication of correct mask fitting is quantised as a degree of leak. The mask leak flow can be compared against a threshold value, representing the no leak degree, to determine whether there is correct mask fitting if the threshold value is not exceeded.

Advantageously, if there has been no previous session the test pressure is chosen to be a base pressure. The percentile pressure can be in a range between the 75$^{th}$ and 95th percentile pressure. Further, the base pressure can be in the range 10–12 cm $H_2O$.

In a preferred form, the ventilatory assistance apparatus can have an automatic pressure mode in which case the respective steps recited above for controller operation are performed, and a manual pressure mode in which the currently set ventilatory assistance pressure is chosen to be the test pressure.

The test pressure can be applied for a period of time, for example 3 minutes.

BRIEF DESCRIPTION OF THE DRAWINGS

An embodiment of the invention now will be described with reference to the accompanying drawings, in which.

DESCRIPTION OF PREFERRED EMBODIMENTS AND BEST MODE

Figure 1:
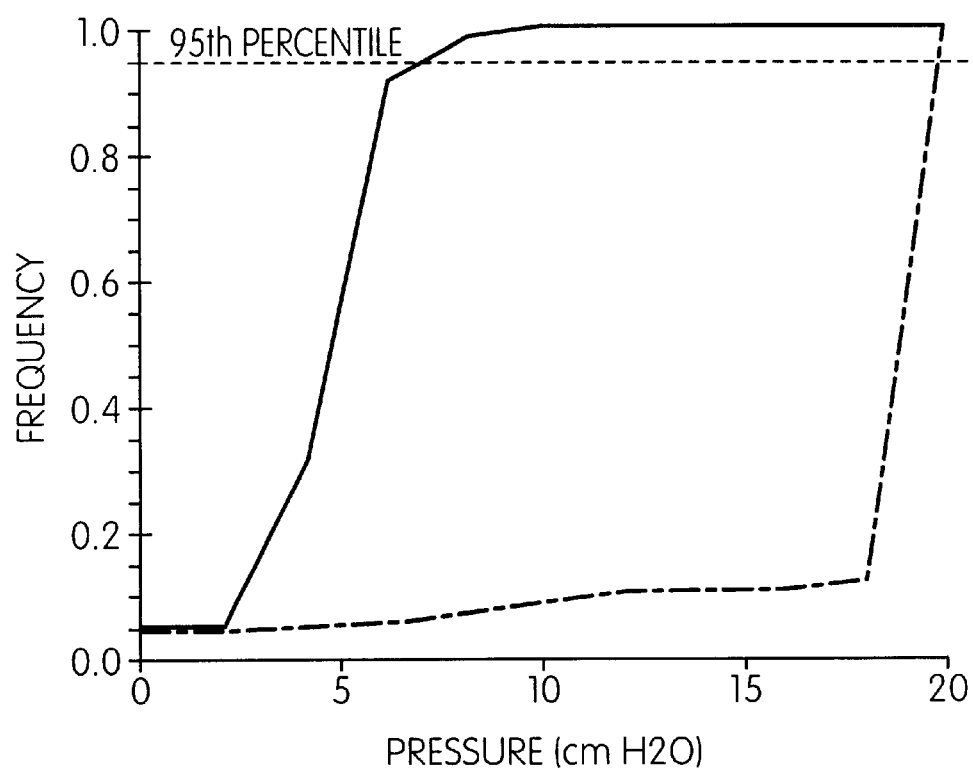
FIG. 1 shows a cumulative frequency plot as a function of treatment pressure for two patients.
Figure 2:
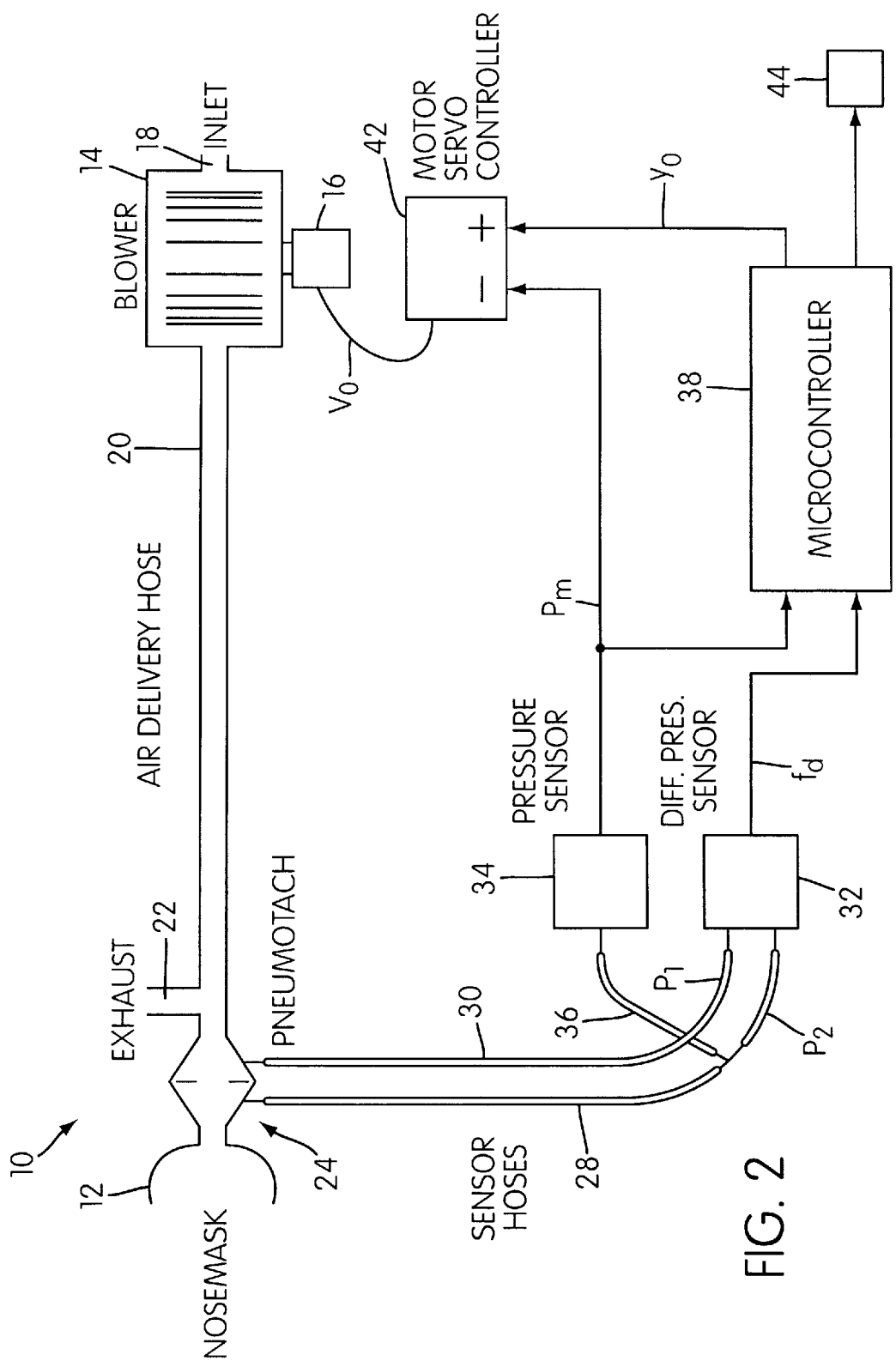
FIG. 2 shows a schematic block diagram of CPAP apparatus.

FIG. 2 shows CPAP treatment apparatus 10, as one form of positive pressure ventilatory assistance, embodying the invention. A turbine/blower 14, operated by a mechanically coupled electrical motor 16, receives air or breathable gas at an inlet 18 thereof, and supplies the breathable gas at a delivery pressure to a delivery tube/hose 20 having connection at the other end thereof with a nose mask 12. Breathable gas thus is provided to the subject's airway for the purpose of providing CPAP treatment, with the subject's expired breath passing to atmosphere by an exhaust 22 in the delivery tube 20, typically located proximate to the mask 12.

Embodiments of the present invention may be used in conjunction with a CPAP device which has two functional modes: "Manual" and "Automatic Titration", and a "Standby" or "Stop" mode. During the Manual mode, the device delivers breathable gases at predetermined pressures. During the Automatic Titration mode, the device delivers breathable gases in the manner described in commonly owned U.S. Pat. No. 5,704,345 (Berthon-Jones, assigned to ResMed Limited referred to above).

Measurement of Flow

A pneumotachograph 24 is placed in the delivery rube 20 between the mask 12 and the exhaust 22 to provide two pressure signals, $P_2$ and $P_1$, across the pneumotachograph, each passed by hoses 28,30 to a differential pressure sensor 32. A determination of the flow of gas in the mask 12 is made the differential pressure, $P_2-P_1$, resulting in a flow signal, $f_d$. The mask pressure, $P_2$, also is passed to a pressure sensor 34 by a tapped line 36 taken from the respective hose 28, to generate a delivery pressure signal, $P_m$, output from The pressure sensor 34.

Both the flow signal, $f_d$, and the pressure signal, $P_m$, are passed to a microcontroller 38 where they are sampled for subsequent signal processing, typically at a rate of 50 Hz.

The microcontroller 38 is programmed to process the flow and pressure signals ($f_d$, $P_m$) to produce an output control signal, $y_0$, provided to an electronic motor servo-controller 42 that, in turn, produces a motor speed control output signal, $V_0$. This signal is provided to the motor 16 to control the rotational speed of the turbine 14 and provide the desired treatment pressure, $P_2$, at the nose mask 12.

The motor servo-controller 42 employs a negative feedback control technique that compares the actual delivery pressure, in the form of the signal $P_m$, with the control signal, $y_0$.

It is equally possible for pressure and/or flow sensors to be located at the blower 14, and the mask pressure and flow values being determined from a knowledge of the blower pressure and the pneumatic characteristics of the hose 20.

Determination of Mask Leak

Figure 3:
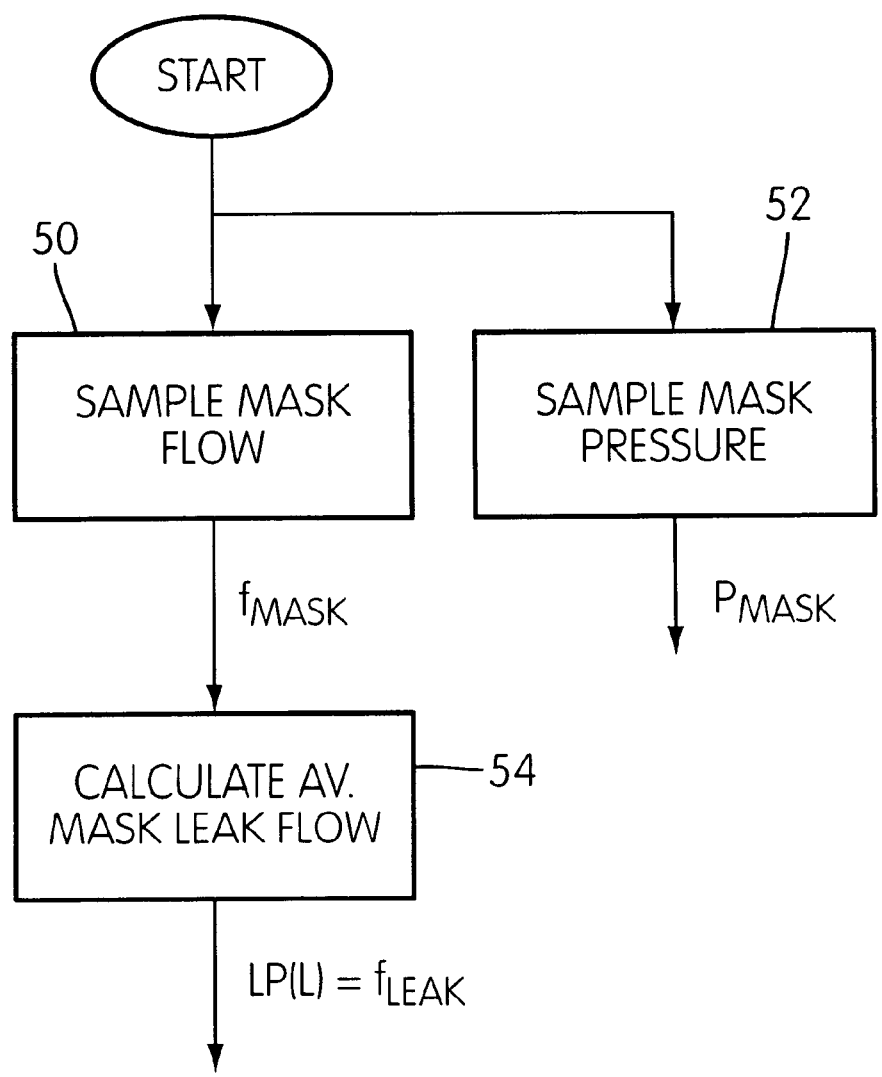
FIG. 3 shows a block flow diagram of calculation of instantaneous leak flow.

Operation of the microcontroller 38 to determine mask leak broadly is as follows. The controlling software resident within the microcontroller 38 performs the following steps in determining the respiratory airflow as broadly described, as also shown in the flow diagram of FIG. 3. Note that the word "average" is used herein in the most general sense of the result of a low pass filtering step, and is not confined to an arithmetic mean.

1. Repeatedly sample the mask airflow, $f_d$, to give a sampled signal, $f_{MASK}$, and the mask pressure, $P_m$, to give a sampled signal, $P_{MASK}$, for example at intervals of T=20 milliseconds. (Steps 50,52).

2. Calculate the average leak, LP(L), which is taken as the leak flow, $f_{LEAK}$ as being the result of low pass filtering the airflow, $f_{MASK}$, with a time constant of 10 seconds (Step 54).

Any other convenient form of determination of leak flow can be utilised, for example, the technique described in international Publication No. WO 98/06440.

Determination of Mask Fitting Pressure and Leak

The determination of correct mask fitting occurs on commencement of a treatment session with the patient in a wake state. The microcontroller 38 has an operational "Mask-Fit" mode that can be entered manually by a patient using pushbutton controls, or automatically. In either case, an initial constant pressure level is applied by the blower 14 to the mask 12. If the functional mode is the Manual mode, then the mask-fit test pressure is the current 'set' pressure. If the functional mode is the Automatic Titration mode, the mask-fit test pressure is the 95th percentile pressure of the previous session—if there was one—otherwise it is the base treatment pressure, e.g. 10–12 cm $H_2O$ This constant pressure is applied for a period of time, typically 1–3 minutes.

During the Mask-Fit mode, the microcontroller 38 continuously determines mask leak as the value, $f_{LEAK}$, as described above, comparing this to a threshold, typically of 0.2 l/s, and providing the patient with a visual indication 44 of degree of leak. This threshold represents the 'no leak' degree. In this way the patient can manipulate the mask to ensure correct fitting as indicated by the appropriate message.

The following algorithm can be used:
  Get the 95th percentile pressure of the most recent
    session, if available.
  If the mode is Automatic Titration
  If the 95th percentile pressure is available & greater than the
    minimum allowable pressure
    Set the pressure to the 95th percentile pressure
  Else
    Set the pressure to the minimum allowable pressure
  End if
  Else if the mode is Manual
    Set the pressure to the current CPAP pressure
  End if
  While in Mask-fit mode
    Check for mask-leak
    Display mask-fit status in terms of **, *, **, * or
      Poor End while In one preferred form, a 'previous session' will only be valid (i.e. "available") if it was of a duration greater than three hours. A representative 'minimum allowable pressure is 10 cmH$_2$O.

The value of P$_{MASK}$ is used in setting and regulating the supplied treatment pressure.

The Mask-Fit mode is exited either 1) when three mites are over; or 2) when the user presses either (i) the Mask-Fit, or (ii) Standby/Start button. If (i), then the device goes back to the previous functional mode. If (ii), then the controller 38 goes back to a stop mode. If the Mask-Fit mode is exited because three minutes have elapsed, the controller 38 goes back to the previous functional mode.

Embodiments of the invention provide the advantage of determining correct mask fitting with greater accuracy than the prior art and thereby improving treatment efficacy. Also, a patient will tend to learn how to fit the mask in a correct manner by observation of a visual indicator on the ventilatory assistance apparatus machine.

Embodiments of the invention may also include the capacity to vary the setting of one or more parameters. For example there may also be provided any one or more of the following:

a) A control to allow for varying the preset period of time that the device remains in the test pressure mode (by either increasing or decreasing that period of time). The control setting may apply every time that the device is used or alternatively apply for the session at which the control is used and then reset to the predetermined setting at the next use session. There may also be provided the capacity vary the time in continuous manner or by increments, say for example, 15 second or one-minute intervals.

b) An override control to stop the test pressure before the expiry of the preset time—there may also be included the choice between either stopping the device or directly selecting the functional mode.

c) A control that allows the varying the determined mask-fit test pressure. The control may allow for the varying of the pressure to be made in a continuous manner or in stepwise manner in suitable increments such as ½ cm H$_2$O or 1 cm H$_2$O increments.

The advantage in incorporating one or more of these controls is to add a degree of user control over the system thereby giving the users (whether clinical staff or patients) a sense of involvement in the course of therapy. These controls also allow for the fine adjustment at the point of therapy (say to achieve a mask strap tension that is slightly greater than is determined appropriate by the invention so as to satisfy a subjective preference of the patient). The flexibility afforded by each of these controls can serve to avoid the need for a service call or attendance of a qualified service personal to adjust the apparatus to suit the unique clinical needs of a patient. It is also envisaged that patient access to any of the controls or the range of variability accessible way of the controls may be limited as required by clinical requirements. This limiting may be appropriate whether the patient is using the apparatus in a home environment without the supervision of clinical personal. Limitation of access to controls might be achieved in any convenient manner, say be incorporation of concealed controls or though microprocessor command controls that are accessible only after input of a secret code.

Although the invention has been described with reference to preferred embodiments, it will be appreciated by those skilled in the art that the invention may be embodied in many other forms. For example, the indication of magnitude or degree of leak can be announced by audible means. Additionally, the test pressure can be in the range of the 75$^{th}$ to the 95$^{th}$ percentile pressure.

We claim:

1. A ventilatory assistance apparatus comprising:

a controllable flow generator providing a positive pressure of breathable gas;

a conduit coupled to the flow generator to receive said gas;

a mask to be worn by a wearer, in turn, to receive said gas from said conduit as a desired pressure; and a controller having a control of said flow generator and programmed to cause a mask-fit test pressure to be applied at the mask, said test pressure being determined as a percentile pressure of a previous ventilatory assistance session.

2. The apparatus of claim 1, further comprising:

flow sensor means, for sensing respiratory flow, passing a flow signal to the controller; and display or indication means; and wherein the controller is further operable to determine mask leak flow at the test pressure from the respiratory flow signal, and to cause the display or indication means to display or otherwise indicate the magnitude of the leak flow as an indication of correct mask fitting.

3. The apparatus of claim 2, wherein the controller further has a manual pressure mode in which a currently set ventilatory assistance pressure is chosen to be applied as the test pressure.

4. The apparatus of claim 3, wherein said controller applies the test pressure for a period of time.

5. The apparatus as claimed in claim 4, wherein said time is three minutes.

6. The apparatus of claim 2, wherein said controller quantises said leak flow to represent a degree of leak.

7. The apparatus of claim 6, wherein the controller is further operable to compare said leak flow against a threshold value representing zero degree of leak, and to determine that there is correct mask fitting if the threshold is not exceeded.

8. The apparatus of claim 7, wherein, if there is no previous percentile pressure available, then the controller determines that a base pressure is to be applied, as said test pressure.

9. The apparatus of claim 8, wherein said percentile pressure is chosen from be range of the 75$^{th}$–95$^{th}$ percentile pressure.

10. The apparatus of claim 9, wherein said base pressure is in the range 10–12 cmH$_2$O.

11. The apparatus of claim 10, wherein said controller is further operable to determine that a previous pressure is available if a previous ventilatory assistance session occurred for greater than a predetermined time interval.

12. The apparatus of claim 11, wherein said predetermined time interval is three hours.

* * * * *